(12) United States Patent
Chen et al.

(10) Patent No.: US 8,636,361 B2
(45) Date of Patent: Jan. 28, 2014

(54) LEARNING-BASED VISUAL ATTENTION PREDICTION SYSTEM AND METHOD THEREOF

(75) Inventors: Homer H. Chen, Taipei (TW); Su-Ling Yeh, Taipei (TW); Tai-Hsiang Huang, Taipei (TW); Wen-Fu Lee, Tainan (TW); Ling-Hsiu Huang, Tainan (TW)

(73) Assignees: National Taiwan University, Taipei (TW); Himax Technologies Limited, Tainan (TW)

( * ) Notice: Subject to any disclaimer, the term of this patent is extended or adjusted under 35 U.S.C. 154(b) by 218 days.

(21) Appl. No.: 13/187,287

(22) Filed: Jul. 20, 2011

(65) Prior Publication Data

US 2013/0021578 A1 Jan. 24, 2013

(51) Int. Cl.
*A61B 3/00* (2006.01)
*A61H 5/00* (2006.01)
*A61B 3/113* (2006.01)

(52) U.S. Cl.
CPC . *A61H 5/00* (2013.01); *A61B 3/113* (2013.01)
USPC .......................... 351/203; 351/209; 351/240

(58) Field of Classification Search
CPC .................................. A61H 5/00; A61B 3/113
USPC ......... 351/200, 203, 205, 209, 210, 237, 239, 351/242, 246, 240; 382/159
See application file for complete search history.

(56) References Cited

U.S. PATENT DOCUMENTS

2010/0086221 A1* 4/2010 Stankiewicz et al. ......... 382/224
2011/0040711 A1* 2/2011 Perronnin et al. .............. 706/12

* cited by examiner

*Primary Examiner* — Huy K Mai
(74) *Attorney, Agent, or Firm* — Stout, Uxa, Buyan & Mullins, LLP

(57) ABSTRACT

A learning-based visual attention prediction method is disclosed. The method includes a correlation relationship between the fixation density and at least one feature information being learned by training, followed by a test video sequence of test frames being received. Afterward, at least one tested feature map is generated for each test frame based on the feature information. Finally, the tested feature map is mapped into a saliency map, which indicates the fixation strength of the corresponding test frame, according to the correlation relationship.

14 Claims, 7 Drawing Sheets

LEARNING-BASED VISUAL ATTENTION PREDICTION SYSTEM AND METHOD THEREOF

BACKGROUND OF THE INVENTION

1. Field of the Invention

The present invention generally relates to visual attention prediction systems and methods, and more particularly to a learning-based visual attention prediction system and method for video signals.

2. Description of Related Art

Visual attention is an important characteristic of the five biological senses. It helps the human brain filter out excessive visual information and enables the eyes to focus on particular regions of interest. Visual attention has been a subject of research in neural science, physiology, psychology, and vision. Data gleaned from these studies can be used not only to greatly enrich current understandings of the psychophysical aspect of visual attention, but also to enhance the processing of the video signals.

The fixation points in an image usually attract the most attention. If the attended regions of the image can be predicted, the video signals of the more attractive regions can be detail-processed and visually more important areas can be better preserved in the coding process. A typical visual attention model consists of two parts: extraction of features and fusion of features. The feature maps are generated after feature extraction from the image, and the feature maps are then fused to form a saliency map by nonlinear fusion, linear fusion with equal weight, or linear fusion with dynamic weight. However, improper weight assignment in the feature fusion process or low-level features alone, such as color, orientation, etc., can result in perceptual mismatches between the estimated salience and the actual human fixation.

For the reason that conventional 3D imaging systems could not effectively predict visual attention, a need has arisen to propose a novel visual attention prediction system and method that can faithfully and easily predict visual attention.

SUMMARY OF THE INVENTION

In view of the foregoing, it is an object of the embodiment of the present invention to provide a learning-based visual attention prediction system and method to predict visual attention effectively.

According to one embodiment, a learning-based visual attention prediction system which comprises a feature extraction unit and a regression model is disclosed. The feature extraction unit receives a test video sequence which comprises a plurality of test frames, and generates at least one tested feature map for each test frame based on at least one feature information. The regression model has a correlation relationship between the fixation density and the feature information. The regression model maps the tested feature maps into a saliency map, which indicates the fixation strength of the corresponding test frame, according to the correlation relationship.

According to another embodiment, a learning-based visual attention prediction method is disclosed. The method comprises the following steps: firstly, a correlation relationship between the fixation density and at least one feature information is learned by training. Then, a test video sequence which comprises a plurality of test frames is received. Afterward, at least one tested feature map is generated for each test frame based on the feature information. Finally, the tested feature map is mapped into a saliency map, which indicates the fixation strength of the corresponding test frame, according to the correlation relationship.

DETAILED DESCRIPTION OF THE INVENTION

Figure 1:
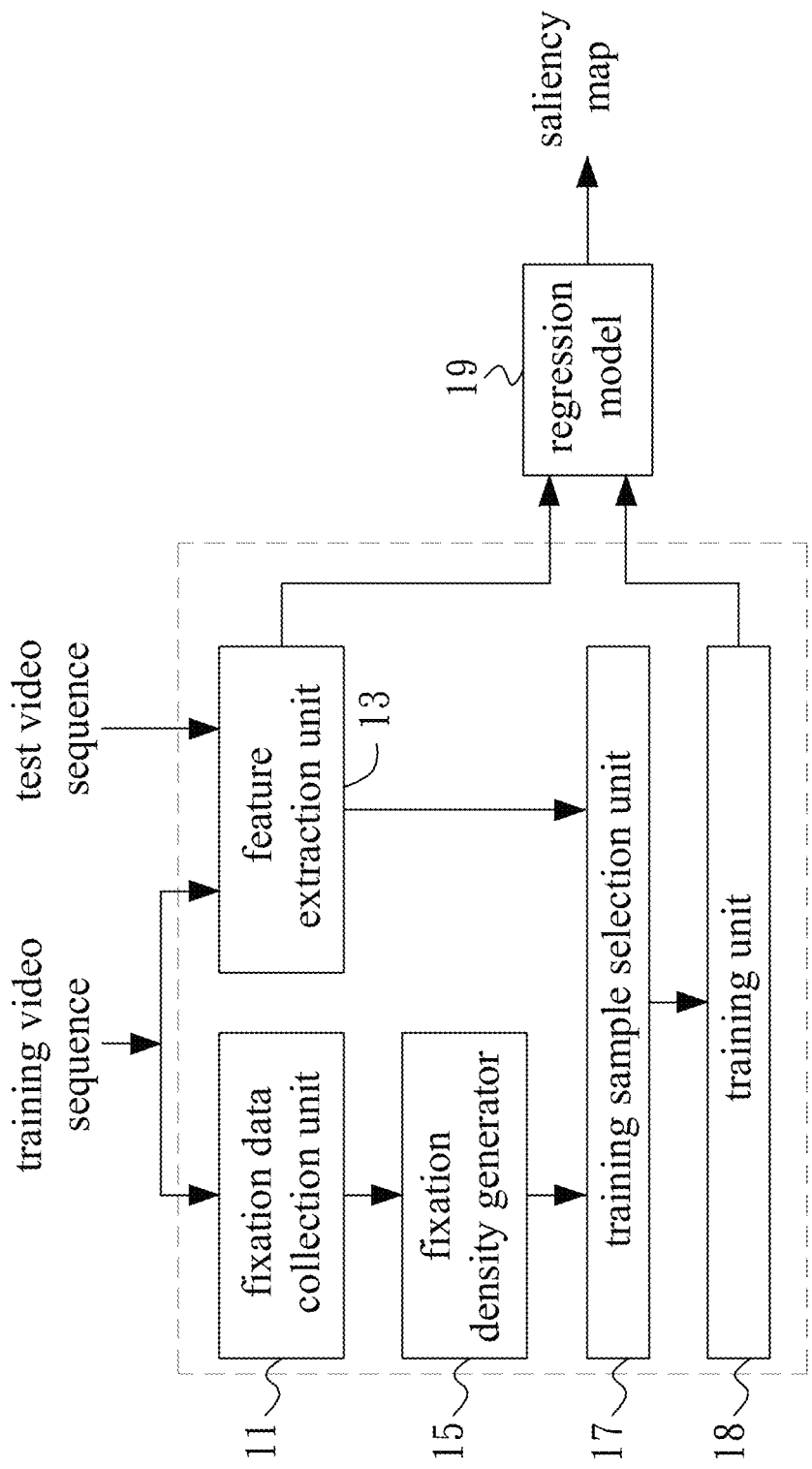
FIG. 1 shows a block diagram illustrating a learning-based visual attention prediction system according to one embodiment of the present invention.

Referring more particularly to the drawings, FIG. 1 shows a block diagram illustrating a learning-based visual attention prediction system according to one embodiment of the present invention. The visual attention prediction system 1 comprises a fixation data collection unit 11, a feature extraction unit 13, a fixation density generator 15, a training sample selection unit 17, a training unit 18, and a regression model 19. The computational scheme of the visual attention prediction system 1 is executed in a training phase and a test phase.

Figure 3:
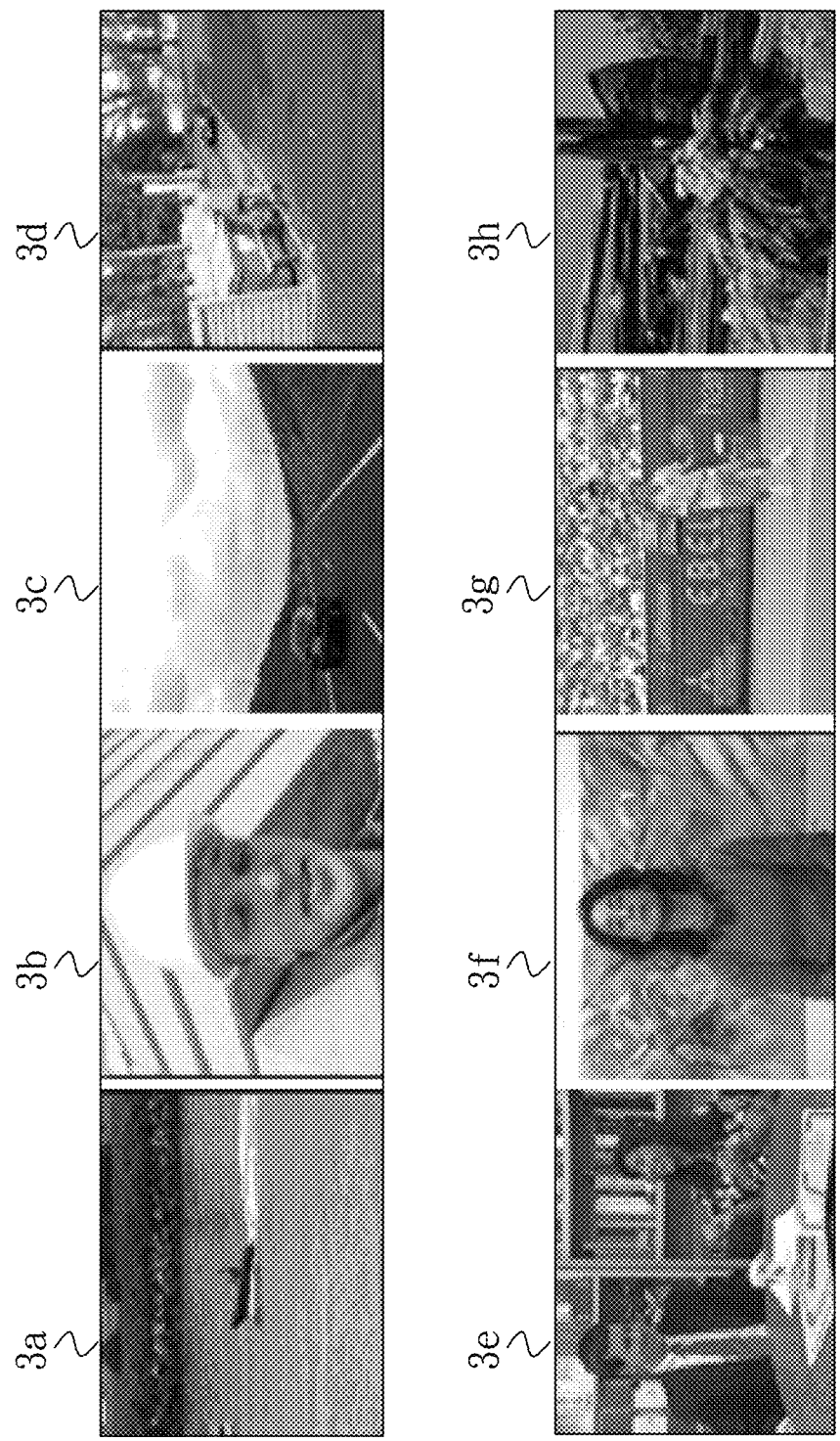
FIG. 3 exemplifies the training video sequences according to one embodiment of the present invention.

During the training phase, it must obtain the training samples and the fixation data from the given training video sequences, and then learn mapping information needed in the test phase. Firstly, the fixation data collection unit 11 receives a plurality of training video sequences 3a-3h, as shown in FIG. 3, and each training video sequence comprises a plurality of training frames. The fixation data collection unit 11 detects a plurality of fixation points gazed in each training frame of the training video sequences 3a-3h, so as to collect all fixation points of each training frame to generate a fixation map.

Figure 2:
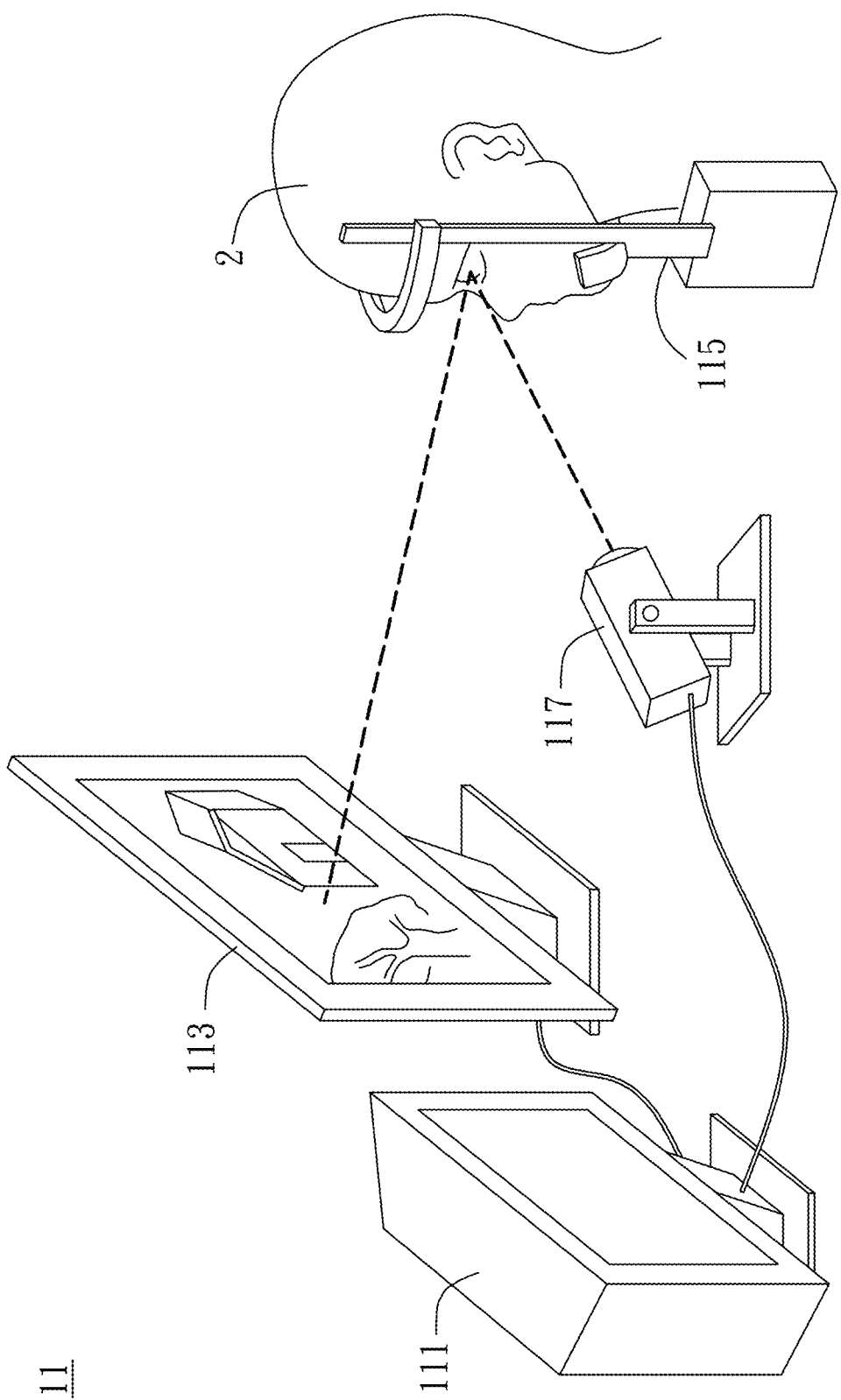
FIG. 2 shows an architecture diagram illustrating an eye tracking system according to one embodiment of the present invention.

Specifically, the fixation data collection unit 11 comprises an eye tracking system, as shown in FIG. 2. The eye tracking system comprises a host PC 111, a displayer 113, a supporting rest (or a chin and forehead rest) 115 and a camera 117. The displayer 113 is configured to display the training video sequences 3a-3h. The supporting rest 115 is configured to support the viewer 2 to watch the training video sequences 3a-3h displayed by the displayer 113. The camera 117 is configured to front the viewer 2 and tracks the eye movement of the viewer 2. The host PC 111, coupled with the displayer 113 and the camera 117, controls the displayer 113 to display the training video sequences 3a-3h and records the fixation points (human fixation data) which the viewer 2 gazes in the training frame. In practice, plural viewers 2 with different backgrounds were invited to participate in the eye tracking experiment, and the training video sequences 3a-3h would be displayed sequentially by the displayer 113. As the viewer's chin and head were well seated on the supporting rest 115, the camera 117 started to detect the position of the current displayed training frame where the viewer 2 gazes (i.e. the fixation points) which are recorded by the host PC 111. Therefore, for each training frame, the fixation points of all viewers are collected to generate a fixation map.

Figure 4:
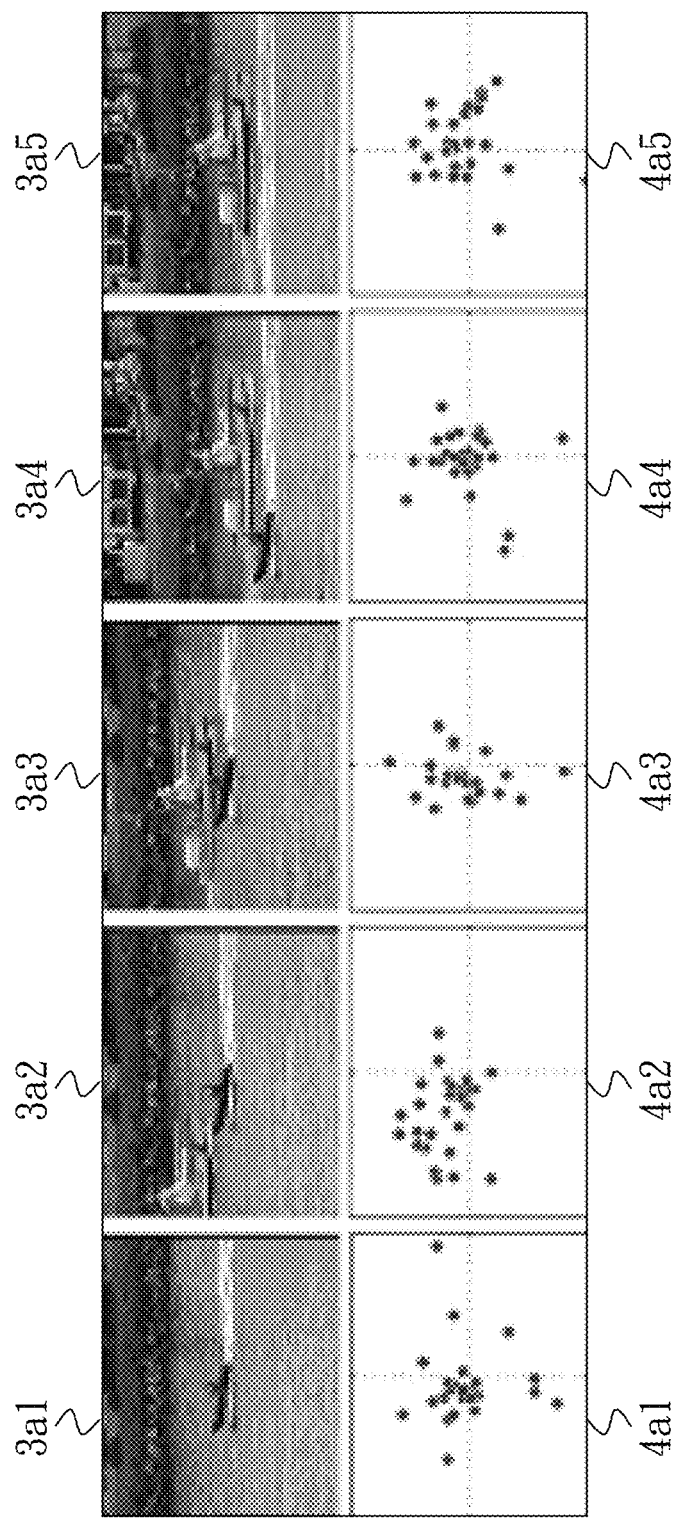
FIG. 4 exemplifies the training frames and the corresponding fixation maps according to one embodiment of the present invention.

With reference to FIG. 4, the training frames and the corresponding fixation maps are elucidated according to one embodiment of the present invention. The training video sequences 3a, for example, consists of plural successive training frames 3a1-3a5. The fixation points of the training frames 3a1-3a5 where the viewers 2 gaze are collected to generate the corresponding fixation maps 4a1-4a5. For example, each fixation point in the fixation maps 4a1 represents the position of the training frames 3a1 where the viewer 2 gazes. The empirical fixation data collected by the eye tracking system from viewers 2 or human subjects are used as the ground truth for training the regression model 19.

Figure 5:
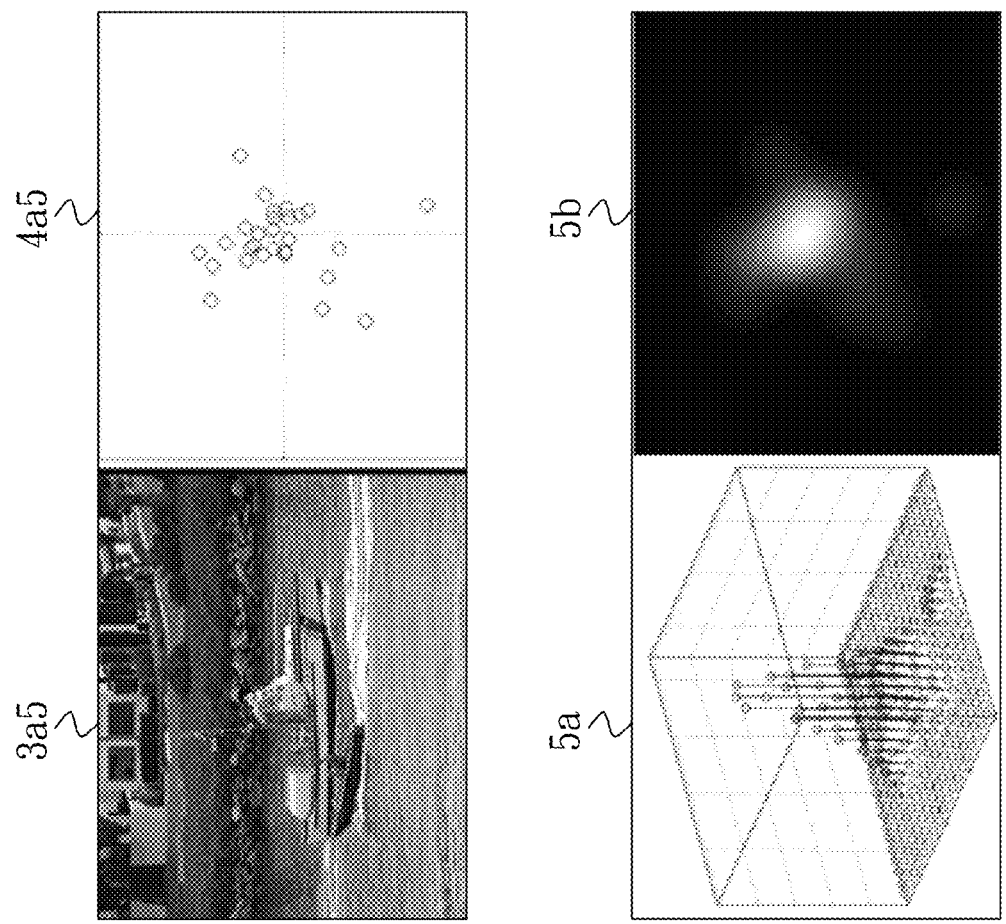
FIG. 5 exemplifies a training frame and the corresponding fixation map and fixation density map according to one embodiment of the present invention.

The fixation density generator 15, coupled to the fixation data collection unit 11, is configured to transform each fixation map into a fixation density map which represents the salience of each training frame. Specifically, the fixation map (e.g. 4a1) generated in the data collection process for each training frame (e.g. 3a1) of any training video sequence (e.g. 3a) is a set of discrete fixation points $\{(x_n^f, y_n^f), n=1, \ldots, N\}$, wherein N represents the number of the viewers 2 participating in the eye tracking experiment. The fixation density generator 15 interpolates the fixation map to make a fixation density map. Please refer to FIG. 5, which exemplifies a training frame and the corresponding fixation map and fixation density map according to one embodiment of the present invention. As shown in FIG. 5, the fixation density generator 15 filters the fixation map 4a5 of the training frame 3a5 with a Gaussian distribution function, yielding equation (1), so as to generate a fixation density map 5b.

$$s(x, y) = \frac{1}{N} \sum_{n=1}^{N} \frac{1}{2\pi\sigma_s^2} \cdot \exp\left(-\frac{(x - x_n^f)^2 + (y - y_n^f)^2}{2\sigma_s^2}\right), \quad (1)$$

Wherein, s(x, y) denotes the fixation density map 5b which carries a fixation density value of each pixel in the training frame 3a5. And $\sigma_s$, the standard deviation of the Gaussian distribution, is determined in accordance with the visual angle accuracy of the eye tracking system, $\sigma_s$=L×tan 0.5π/180, where L is the viewing distance between the viewer 2 and the displayer 113. We can see from equation (1) that the fixation density is estimated by taking the Gaussian weighted average of the fixation values. In this way, each fixation pixel propagates its value to nearby pixels. Therefore, a pixel in a densely populated fixation area is more attractive than a pixel in a sparsely populated fixation area. FIG. 5a, which is the 3D view of the fixation density map 5b, indicates the fixation strength distribution of each pixel.

The feature extraction unit 13 receives the training video sequences 3a-3h one by one and extracts the features of each training frame. The feature extraction takes into account what kind of feature in the image attracts human attention. Based on three low-level feature information, such as color, motion, and orientation information of the video frame and one high-level feature information, such as face, the feature extraction unit 13 generates four corresponding training feature maps, such as the color feature map, motion feature map, orientation feature map, and face feature map, for each training frame of the training video sequences 3a-3h.

The training feature map carries a training feature value of each pixel in the corresponding training frame. Specifically, according to color contrast, the color feature map denotes the degree of attraction of each pixel (or block) in the image. The motion feature map denotes the relative motion of each pixel (or block) in the image. The larger the motion contrast, the stronger the response of the neural cells. The contrast of orientation, which is obtained by computing the difference of the two local orientation images, forms the orientation feature map. And the human face in the image may be detected to form the face feature map. The face detector may be implemented by a suitable conventional technique, for example, as disclosed in "Face Detection using Local SMQT Features and Split Up SNoW Classifier" by Nilsson et al., the disclosure of which is hereby incorporated by reference.

In the embodiment of the present invention, for each training frame (e.g. 3a1) of any training video sequences (e.g. 3a), the feature extraction unit 13 generates four feature maps and the fixation density generator 15 generates one corresponding fixation density map. After obtaining the above information generated in training phase, the training unit 18 can train the regression model 19 according to the correlation relationship between the fixation density and the feature information of each pixel, so as to enter into a test phase later. However, if using all and huge amount of correlation relationships between the fixation density and the feature information of all pixels to train the regression model 19, it is time consuming and inefficient. Therefore, before entering into the test phase, the training sample selection unit 17 selects the training samples for regressor training. Specifically, each training sample is represented as a quintuplet of data consisting of a fixation density value and four corresponding feature values of a pixel.

The training sample selection unit 17, coupled to the training unit 18, is configured to select at least one sample frame among the training frames of each training video sequence. The density of the fixation points of the selected sample frame should be most dense in a specific scene. Specifically, since the spatial fixation distribution of a training frame reflects the degree of attention of the training frame, the training sample selection unit 17 finds the centroid of the fixation points for each training frame of a training video sequence and calculates the mean of the distance between each fixation point and the centroid. The frame with the smallest mean is selected as the sample frame for representing the training video sequence in the specific scene. One may, but is not limited to, select more than one sample frame from each training video sequence.

In another embodiment, the training sample selection unit 17 selects a relatively small number of pixels from each sample frame as the sample pixels. The selected sample pixels are the fixation points where in relatively dense region of the fixation density map of the sample frame. Once the sample pixels are selected, the training unit 18 will train the regression model 19 according to mapping relationship between the fixation density values of the sample pixels and the training feature values of the sample pixels.

After the training samples are obtained, the regression model 19 is trained to learn the correlation relationship between the fixation density and the features information of the training samples. In one embodiment, the training unit 18 adopts the support vector regression (SVR) algorithm to train the regression model 19. Besides learning the correlation relationship between the fixation density and the features information by receiving plural training video sequence real time, the correlation relationship can be pre-built in the regression model 19. In practice, the feature extraction unit 13 receives a test video sequence which comprises a plurality of test frames, and generates four tested feature maps for each test frame based on four corresponding feature information. Then, the regression model 19 maps the tested feature maps into a saliency map, which indicates the fixation strength of the corresponding test frame, according to the trained correlation relationship. The saliency map, similar to the fixation density map 5*b*, has a saliency region with relatively large fixation strength which is prediction of visual attention. Therefore, it needs to perform relatively detailed image process on the portion of test frame which corresponds to the saliency region.

Figure 6A:
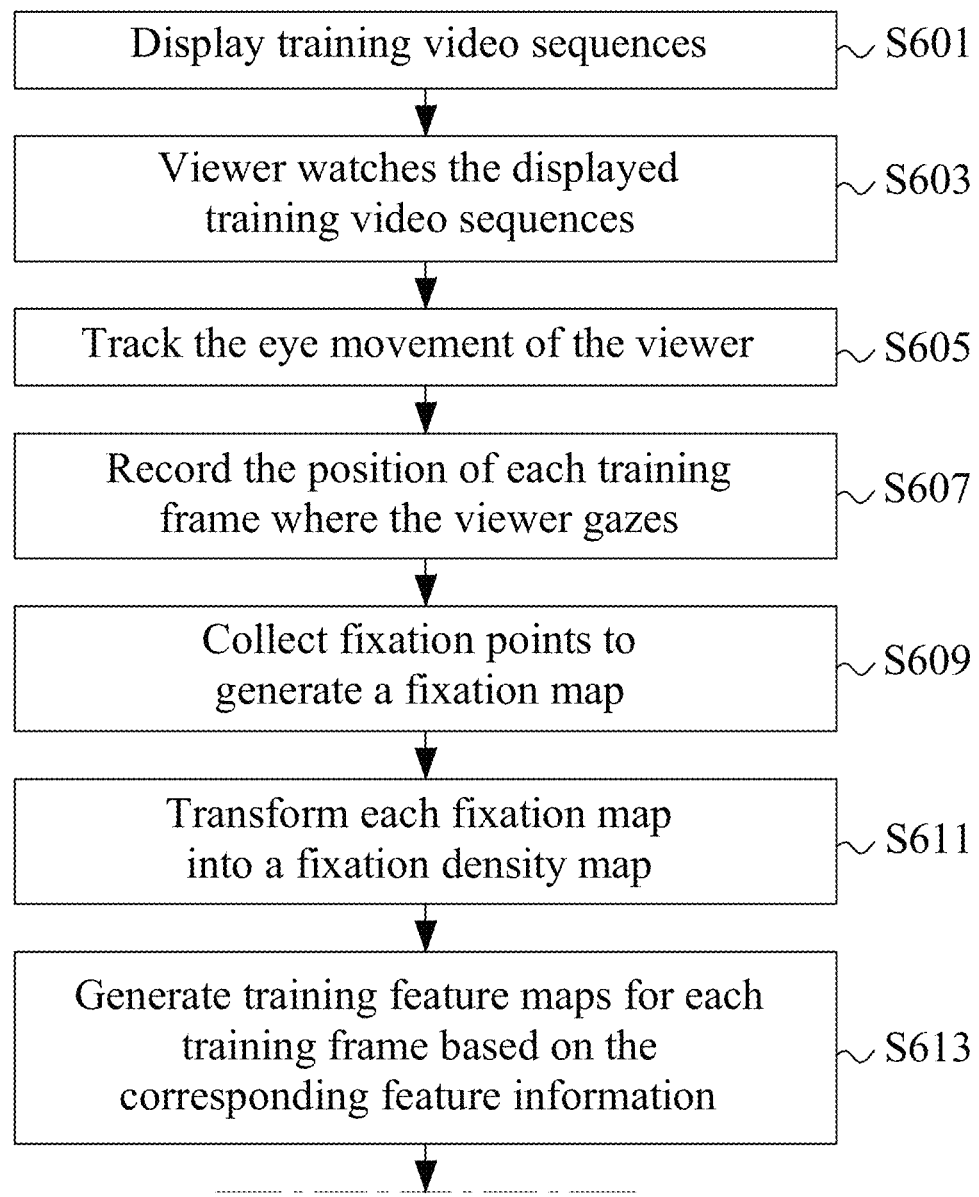
FIG. 6 shows a flow diagram illustrating a learning-based visual attention prediction method according to one embodiment of the present invention.
Figure 6B:
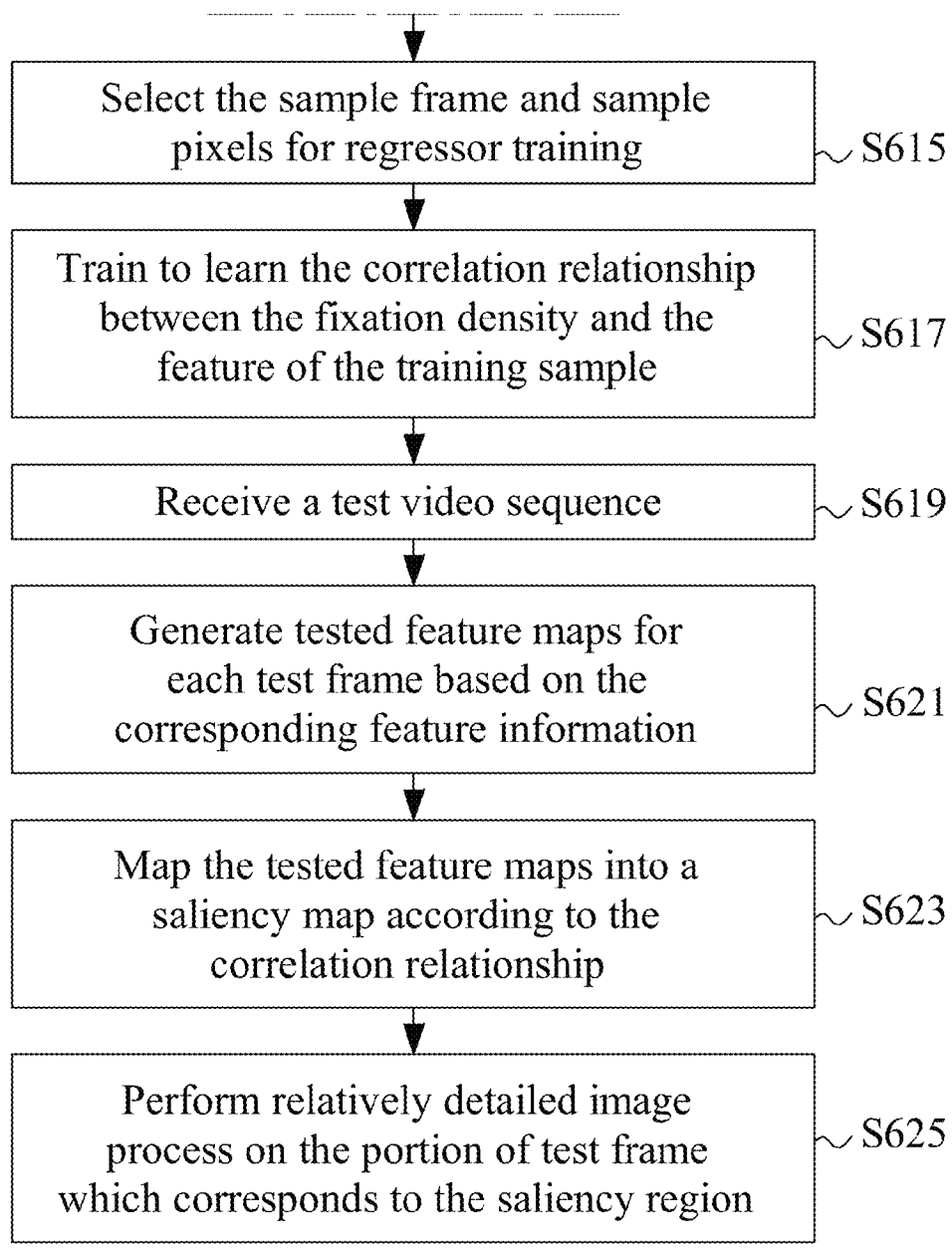

FIG. 6 shows a flow diagram illustrating a learning-based visual attention prediction method according to one embodiment of the present invention. Firstly, plural viewers 2 were invited to participate in the eye tracking experiment to collect fixation data. In step S601, the host PC 111 controls the displayer 113 to display the training video sequences 3*a*-3*h* sequentially, and the viewers 2 watch the displayed training video sequences 3*a*-3*h* in step S603. Simultaneously, the camera tracks the eye movement of the viewers 2 in step S605, and then the host PC 111 records the position of each training frame where the viewers 2 gaze in step S607.

Afterward, in step S609, for each training frame, the detected fixation points from the viewers 2 are collected to generate a fixation map. In step S611, the fixation density generator 15 transforms each fixation map into a fixation density map. In step S613, the feature extraction unit 13 generates four training feature maps (i.e. the color feature map, motion feature map, orientation feature map, and face feature map) for each training frame of the training video sequences 3*a*-3*h* based on the four corresponding feature information. In order to reduce computation, the training sample selection unit 17 selects one sample frame from each training video sequence and selects plural sample pixels from the selected sample frame for regressor training in step S615.

After obtaining the training samples, the training unit 18 trains the regression model 19 to learn the correlation relationship between the fixation density and the feature information according to mapping relationship between the fixation density maps and the training feature maps of the training samples in step S617. And the work in training phase is finished. It is noted that the correlation relationship between the fixation density and the feature information not only can be real time generated by above steps, but also can be pre-built in the regression model 19 to avoid time consuming of pre-process.

After obtaining the correlation relationship between the fixation density and the feature information, it is time to enter into the test phase. In step S619, the feature extraction unit 13 receives a test video sequence and generates four tested feature maps for each test frame of the test video sequence based on the four corresponding feature information in step S621. Finally, in step S623, the regression model 19 maps the tested feature maps into a saliency map according to the trained correlation relationship, so as to predict the region of visual attention of each test frame. In step S625, the processor (not shown) performs relatively detailed image process on the portion of test frame which corresponds to the saliency region in the saliency map.

According to the foregoing embodiment, the present invention proposes a learning-based visual attention prediction system and method thereof for video signals to provide a computation scheme that firstly obtains the correlation relationship between the fixation density and the feature information in training phase, and then uses the correlation relationship to train the regression model 19 in test phase. It predicts visual attention based on machine learning to determine the relationship between visual attention and the features, so as to avoid perceptual mismatch between the estimated salience and the actual human fixation.

Although specific embodiments have been illustrated and described, it will be appreciated by those skilled in the art that various modifications may be made without departing from the scope of the present invention, which is intended to be limited solely by the appended claims.

What is claimed is:

1. A learning-based visual attention prediction system, comprising:
   a fixation data collection unit configured to receive a plurality of training video sequences which comprises a plurality of training frames and configured to detect a plurality of fixation points gazed in each of the plurality of training frames of the plurality of training video sequences and collect the fixation points to generate a fixation map for each of the plurality of training frames; and
   a fixation density generator, coupled to the fixation data collection unit, configured to transform each of the fixation maps into a fixation density map which carries a fixation density value for every pixel in the corresponding training frame;
   a feature extraction unit configured to receive a test video sequence which comprises a plurality of test frames and generate at least one tested feature map for each test frame based on at least one feature information, wherein the feature information comprises color, motion, orientation, or face;
   a regression model, having a correlation relationship between fixation density and the feature information, configured to map the at least one tested feature map into a saliency map based on the correlation relationship, wherein the saliency map indicates fixation strength of the test frame based on the fixation density; and
   a training unit configured to train the regression model to learn the correlation relationship between the fixation density and the feature information;
   wherein the feature extraction unit further receives the training video sequences and generates at least one training feature map for each of the plurality of training frames of the training video sequences based on the at least one feature information, and the training unit trains the regression model according to the fixation density maps and the training feature map; and
   wherein the motion feature information denotes a relative motion of each pixel or block in an image and the orientation feature information is formed from a contrast of orientation obtained by computing a difference of two local orientation images.

2. The system of claim 1, further comprising:
   a training sample selection unit, coupled to the training unit, configured to select at least one sample frame among the training frames of each training video sequence, wherein the density of the fixation points of the selected sample frame is most dense.

3. The system of claim 2, wherein the training sample selection unit selects a plurality of sample pixels from the sample frame, wherein the selected sample pixels are the fixation points where in relatively dense region of the fixation density map of the sample frame.

4. The system of claim 3, wherein the at least one training feature map carries a training feature value of each pixel in the corresponding training frame, and the training unit trains the regression model according to mapping relationship between the fixation density values of the sample pixels and the training feature values of the sample pixels.

5. The system of claim 1, wherein the system is configured to enable a plurality of viewers to perform experimenting sequentially for obtaining the correlation relationship by the fixation data collection unit, which comprises:
- a displayer configured to display the training video sequences;
- a supporting rest configured to support the viewer under experiment to watch the training video sequences displayed by the displayer;
- a camera, fronting the viewer under experiment, configured to track the eye movement of the viewer under experiment; and
- a host PC, coupled with the displayer and the camera, configured to control the displayer to display the training video sequences and record the positions where the viewer under experiment gaze in the training frames;
- wherein, the positions where the viewer under experiment gaze in the training frames are the fixation points.

6. The system of claim 1, wherein the training unit adopts the support vector regression (SVR) algorithm to train the regression model.

7. The system of claim 1, wherein the saliency map has a saliency region with relatively large fixation strength.

8. A learning-based visual attention prediction method, comprising:
- learning a correlation relationship between the fixation density and at least one feature information by training, wherein the step of learning the correlation relationship comprises:
  - receiving a plurality of training video sequences which comprises a plurality of training frames;
  - detecting a plurality of fixation points gazed in each of the plurality of training frames of the plurality of training video sequences;
  - collecting the fixation points to generate a fixation map for each of the plurality of training frames;
  - transforming each of the fixation maps into a fixation density map;
  - generating at least one training feature map for each of the plurality of training frames of the training video sequences based on the at least one feature information; and
  - learning the correlation relationship according to the fixation density maps and the training feature map;
- receiving a test video sequence which comprises a plurality of test frames;
- generating at least one tested feature map for each test frame based on the at least one feature information, wherein the feature information comprises color, motion, orientation, or face; and
- mapping the tested feature map into a saliency map based on the correlation relationship, wherein the saliency map indicates fixation strength of the test frame based on the fixation density;
- wherein the motion feature information denotes a relative motion of each pixel or block in an image and the orientation feature information is formed from a contrast of orientation obtained by computing a difference of two local orientation images.

9. The method of claim 8, wherein the step of learning the correlation relationship further comprises:
- selecting at least one sample frame among the training frames of each training video sequence, wherein the density of the fixation points of the selected sample frame is most dense; and
- selecting a plurality of sample pixels from the sample frame, wherein the selected sample pixels are the fixation points where in relatively dense region of the fixation density map of the sample frame.

10. The method of claim 9, wherein the fixation density map carries a fixation density value for every pixel in the corresponding training frame and the training feature map carries a training feature value of each pixel in the corresponding training frame, and the step of learning the correlation relationship further comprises:
- learning the correlation relationship according to mapping relationship between the fixation density values of the sample pixels and the training feature values of the sample pixels.

11. The method of claim 8, wherein a plurality of viewers perform experimenting sequentially for obtaining the correlation relationship, and the step of detecting the fixation points further comprises:
- displaying the training video sequences;
- supporting the viewer under experiment to watch the displayed training video sequences;
- tracking the eye movement of the viewer under experiment; and
- recording the positions where the viewer under experiment gaze in the training frames;
- wherein, the positions where the viewer under experiment gaze in the training frames are the fixation points.

12. The method of claim 8, adopting the support vector regression (SVR) algorithm to train and learn the correlation relationship.

13. The method of claim 8, wherein the saliency map has a saliency region with relatively large fixation strength.

14. The method of claim 13, further comprising:
- performing relatively detailed image process on the portion of the test frame which corresponds to the saliency region.

* * * * *